United States Patent
Morita (10) Patent No.: US 10,307,168 B2
(45) Date of Patent: Jun. 4, 2019

(54) COMPLEX COIL AND MANUFACTURING TECHNIQUES

(71) Applicant: Terumo Corporation, Tokyo (JP)

(72) Inventor: Hideo Morita, Irvine, CA (US)

(73) Assignee: Terumo Corporation, Tokyo (JP)

(*) Notice: Subject to any disclaimer, the term of this patent is extended or adjusted under 35 U.S.C. 154(b) by 268 days.

(21) Appl. No.: 15/231,539

(22) Filed: Aug. 8, 2016

(65) Prior Publication Data
US 2017/0035436 A1    Feb. 9, 2017

Related U.S. Application Data

(60) Provisional application No. 62/202,649, filed on Aug. 7, 2015.

(51) Int. Cl.
*A61B 17/00* (2006.01)
*A61B 17/12* (2006.01)
*A61F 6/22* (2006.01)
*A61B 90/00* (2016.01)

(52) U.S. Cl.
CPC .. *A61B 17/12145* (2013.01); *A61B 17/12113* (2013.01); *A61F 6/22* (2013.01); *A61B 2017/00526* (2013.01); *A61B 2017/00632* (2013.01); *A61B 2017/00641* (2013.01); *A61B 2017/00867* (2013.01); *A61B 2017/00898* (2013.01); *A61B 2090/3966* (2016.02)

(58) Field of Classification Search
CPC ........ A61B 17/12145; A61B 17/12113; A61B 17/12022; A61B 17/1214; A61B 17/12163; A61B 2017/00867; A61B 17/12172
See application file for complete search history.

(56) References Cited

U.S. PATENT DOCUMENTS

| | | | |
|---|---|---|---|
| 1,594,292 | A | 7/1926 | Zierick |
| 1,645,941 | A | 10/1927 | Williams |
| 1,653,951 | A | 12/1927 | Featherstone |
| 2,296,356 | A | 9/1942 | Lindenblad |
| 2,825,169 | A | 3/1958 | Ciroli |
| 3,154,457 | A | 10/1964 | Ranoha |
| 3,482,126 | A | 12/1969 | Bradley |
| 4,551,132 | A | 11/1985 | Pásztor et al. |
| 4,663,358 | A | 5/1987 | Hyon et al. |
| 4,739,768 | A | 4/1988 | Engelson |

(Continued)

FOREIGN PATENT DOCUMENTS

| | | |
|---|---|---|
| DE | 19647280 A1 | 11/1996 |
| EP | 0739605 B1 | 8/1998 |

(Continued)

OTHER PUBLICATIONS

Anderson, James H., Sidney Wallace, and Cesare Gianturco, *Transcatheter Intravascular Coil Occlusion of Experimental Arteriovenous Fistulas*, A. J. Proentgenol. 129:795-798, Nov. 1977.

(Continued)

*Primary Examiner* — Katrina M Stransky
(74) *Attorney, Agent, or Firm* — Inskeep IP Group, Inc.

(57) ABSTRACT

An embolic coil which can be used for occlusive purposes in the vasculature is described. A mandrel for manufacturing a coiled structure, and method/process for manufacturing a coiled structure is described.

12 Claims, 6 Drawing Sheets

(56) References Cited

U.S. PATENT DOCUMENTS

| | | |
|---|---|---|
| 4,795,741 A | 1/1989 | Leshchiner et al. |
| 4,819,637 A | 4/1989 | Dormandy, Jr. et al. |
| 4,884,579 A | 12/1989 | Engelson |
| 4,957,501 A | 9/1990 | Lahille et al. |
| 4,994,069 A | 2/1991 | Ritchart et al. |
| 5,108,407 A | 4/1992 | Geremia et al. |
| 5,122,136 A | 6/1992 | Guglielmi et al. |
| 5,133,731 A | 7/1992 | Butler et al. |
| 5,226,911 A | 7/1993 | Chee et al. |
| 5,234,437 A | 8/1993 | Sepetka |
| 5,258,042 A | 11/1993 | Mehta |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,314,444 A | 5/1994 | Gianturco |
| 5,342,387 A | 8/1994 | Summers |
| 5,350,397 A | 9/1994 | Palermo et al. |
| 5,350,398 A | 9/1994 | Pavcnik et al. |
| 5,382,259 A | 1/1995 | Phelps et al. |
| 5,382,260 A | 1/1995 | Dormandy, Jr. et al. |
| 5,413,791 A | 5/1995 | Rhee et al. |
| 5,423,829 A | 6/1995 | Pham et al. |
| 5,476,472 A | 12/1995 | Dormandy, Jr. et al. |
| 5,522,822 A | 6/1996 | Phelps et al. |
| 5,522,836 A | 6/1996 | Palermo |
| 5,525,334 A | 6/1996 | Ito et al. |
| 5,527,338 A | 6/1996 | Purdy |
| 5,536,274 A | 7/1996 | Neuss |
| 5,549,624 A | 8/1996 | Mirigian et al. |
| 5,578,074 A | 11/1996 | Mirigian |
| 5,580,568 A | 12/1996 | Greff et al. |
| 5,582,619 A | 12/1996 | Ken |
| 5,624,461 A | 4/1997 | Mariant |
| 5,639,277 A | 6/1997 | Mariant et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,676,697 A | 10/1997 | McDonald |
| 5,690,667 A | 11/1997 | Gia |
| 5,690,671 A | 11/1997 | McGurk et al. |
| 5,700,258 A | 12/1997 | Mirigian et al. |
| 5,718,711 A | 2/1998 | Berenstein et al. |
| 5,725,546 A | 3/1998 | Samson |
| 5,749,891 A | 5/1998 | Ken et al. |
| 5,766,219 A | 6/1998 | Horton |
| 5,797,953 A | 8/1998 | Tekulve |
| 5,814,062 A | 9/1998 | Sepetka et al. |
| 5,868,754 A | 2/1999 | Levine et al. |
| D407,818 S | 4/1999 | Mariant et al. |
| 5,891,058 A | 4/1999 | Taki et al. |
| 5,895,378 A | 4/1999 | Nita |
| 5,909,130 A | 6/1999 | Martin et al. |
| 5,911,731 A | 6/1999 | Pham et al. |
| 5,911,737 A | 6/1999 | Lee et al. |
| 5,935,148 A | 8/1999 | Villar et al. |
| 5,957,948 A | 9/1999 | Mariant |
| 5,980,514 A | 11/1999 | Kupiecki et al. |
| 5,989,242 A | 11/1999 | Saadat et al. |
| 6,004,448 A | 12/1999 | Ken et al. |
| 6,010,498 A | 1/2000 | Guglielmi |
| 6,013,084 A | 1/2000 | Ken et al. |
| 6,015,424 A | 1/2000 | Rosenbluth et al. |
| D421,304 S | 2/2000 | Mariant et al. |
| 6,022,369 A | 2/2000 | Jacobsen et al. |
| 6,024,765 A | 2/2000 | Wallace et al. |
| 6,033,423 A | 3/2000 | Ken et al. |
| 6,063,100 A | 5/2000 | Diaz et al. |
| 6,068,644 A | 5/2000 | Lulo et al. |
| D427,680 S | 7/2000 | Mariant et al. |
| 6,090,125 A | 7/2000 | Horton |
| 6,096,034 A | 8/2000 | Kupiecki et al. |
| 6,102,933 A | 8/2000 | Lee et al. |
| 6,165,194 A | 12/2000 | Denardo |
| 6,165,198 A | 12/2000 | McGurk et al. |
| 6,171,326 B1 | 1/2001 | Ferrera et al. |
| 6,176,240 B1 | 1/2001 | Nikolchev et al. |
| 6,193,728 B1 | 2/2001 | Ken et al. |
| RE37,117 E | 3/2001 | Palermo |
| 6,231,586 B1 | 5/2001 | Mariant |
| 6,280,457 B1 | 8/2001 | Wallace et al. |
| 6,322,567 B1 | 11/2001 | Mittelstadt et al. |
| 6,322,576 B1 | 11/2001 | Wallace et al. |
| 6,478,773 B1 | 11/2002 | Gandhi et al. |
| 6,500,190 B2 | 12/2002 | Greene, Jr. et al. |
| 6,585,756 B1 | 7/2003 | Strecker |
| 6,589,265 B1 | 7/2003 | Palmer et al. |
| 6,602,261 B2 | 8/2003 | Greene, Jr. et al. |
| 6,605,101 B1 | 8/2003 | Schaefer et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,656,218 B1 | 12/2003 | Denardo et al. |
| 6,860,893 B2 | 3/2005 | Wallace et al. |
| 6,929,654 B2 | 8/2005 | Teoh et al. |
| 6,984,240 B1 | 1/2006 | Ken et al. |
| 6,990,729 B2 | 1/2006 | Pleskach et al. |
| 7,029,486 B2 | 4/2006 | Schaefer et al. |
| 7,033,374 B2 | 4/2006 | Schaefer et al. |
| 7,066,904 B2 | 6/2006 | Rosenthal et al. |
| 7,107,666 B2 | 9/2006 | Hiatt et al. |
| 7,229,454 B2 | 6/2007 | Tran et al. |
| 7,331,974 B2 | 2/2008 | Schaefer et al. |
| 7,608,086 B2 | 10/2009 | Tanaka et al. |
| 9,089,405 B1 * | 7/2015 | Gulachenski .... A61B 17/12113 |
| 2002/0019647 A1 | 2/2002 | Wallace et al. |
| 2002/0107534 A1 | 8/2002 | Schaefer et al. |
| 2002/0128671 A1 | 9/2002 | Wallace et al. |
| 2003/0005569 A1 | 1/2003 | Hiatt et al. |
| 2003/0120302 A1 | 6/2003 | Minck, Jr. et al. |
| 2005/0192618 A1 | 9/2005 | Porter |
| 2005/0192621 A1 | 9/2005 | Wallace et al. |
| 2013/0131711 A1 | 5/2013 | Bowman |

FOREIGN PATENT DOCUMENTS

| | | |
|---|---|---|
| JP | H0466235 A | 3/1992 |
| JP | 7155331 | 6/1995 |
| JP | 8317992 | 12/1996 |
| JP | 2005-152586 A | 6/2005 |
| WO | WO1990/09893 A2 | 9/1990 |
| WO | WO 1994/009705 A1 | 5/1994 |
| WO | WO9411051 A1 | 5/1994 |
| WO | WO9802100 A1 | 1/1998 |
| WO | WO9817183 A1 | 4/1998 |
| WO | WO 99/09893 A1 | 3/1999 |
| WO | WO 00/21443 A1 | 4/2000 |
| WO | WO 00/74577 A1 | 12/2000 |
| WO | WO 2000/074577 A1 | 12/2000 |
| WO | WO 01/45571 A1 | 6/2001 |
| WO | WO 01/93780 A2 | 12/2001 |
| WO | WO 02/32325 A1 | 4/2002 |
| WO | WO 03/039376 A1 | 5/2003 |

OTHER PUBLICATIONS

Cloft, H.J. et al., "Use of Three-dimensional Guglielmi Detachable Coils in the Treatment of Wide-necked Cerebral Aneurysms," *American Journal of Neuroradiology*, vol. 21, Aug. 2000, 3 pages.

Tan, C.B. et al., "The Feasibility of Three-Dimensional Guglielmi Detachable Coil for Embolisation of Wide Neck Cerebral Aneurysms," *Interventional Neuroradiology*, vol. 6, 2000, 6 pages.

Malek, A.M., et al., "Treatment of an Intracranial Aneurysm Using a New Three-Dimensional-Shape Guglielmi Detachable Coil: Technical Case Report," *Neurosurgery*, vol. 44, No. 5, May 1999, 4 pages.

Yang, P.J., et al., "Platinum Wire: A New Transvascular Embolic Agent," *American Journal of Neuroradiology*, vol. 9, No. 3, American Society of Neuroradiology, Jun. 1988, 4 pages.

Lund, G., et al., "Detachable Steel Spring Coils for Vessel Occlusion," *Radiology*, vol. 155, 1985, 4 pages.

(56) References Cited

OTHER PUBLICATIONS

Brunelle, F., et al., ""Micro" Stainless Steel Coils for Transcatheter Vascular Occlusion in Children," *Pediatric Radiology*, vol. 13, 1983, 3 pages.

Anderson, J., et al., ""Mini" Gianturco Stainless Steel Coils for Transcatheter Vascular Occlusion," *Radiology*, vol. 132, Aug. 1979, 3 pages.

Gianturco, C., et al., "Mechanical Devices for Arterial Occlusion," *American Journal of Roentgenology*, vol. 124, No. 3, Jul. 1975, 8 pages.

\* cited by examiner

Figure 9 ent and elucidated from the following description of

COMPLEX COIL AND MANUFACTURING TECHNIQUES

RELATED APPLICATIONS

This application claims priority to U.S. Provisional Application Ser. No. 62/202,649 filed Aug. 7, 2015 entitled Complex Coil, which is hereby incorporated herein by reference in its entirety.

BACKGROUND OF THE INVENTION

An apparatus and method for embolizing a target site in the vasculature is described.

Vessel occlusion is often necessary in a variety of cases including, but not limited to, treatment of aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature. One method of vessel occlusion involves filling the vessel, malformation, or aneurysm with coils for the purposes of embolization. Such coils may be referred to as embolic coils. Due to the complex geometries associated with the vasculature, it is often difficult to have a coil that can quickly and efficiently occlude the target space. In this regard, embolic coils are often imparted with a secondary shape to improve occlusion and help prevent the coil from migrating out of the target space.

The process of imparting a secondary shape on an embolic coil typically involves winding the coil on a mandrel and applying heat such that the coil takes on the desired shape. This can often be a time consuming process. Manufacturing coils of various sizes can be challenging since the coils are often individually wound on different mandrels or on different regions of a mandrel in order to produce coils of various sizes and/or shapes.

It is therefore desirable to have an embolic coil that can efficiently occlude a target region. It is also desirable to have a process whereby multiple embolic coils can be wound on a common mandrel, or where multiple embolic coils can be produced by winding a single coil on a common mandrel and then cutting the single coil to create multiple, separate coils.

SUMMARY OF THE INVENTION

An embolic coil is described. The embolic coil can be used to occlude a target region of the vasculature.

In one embodiment, the coil includes one or more windings in a first plane and one or more windings in a second plane.

In one embodiment, the coil includes two or more windings in a first plane and two or more windings in a second plane.

In one embodiment, the coil includes two or more windings in a first plane and two or more windings in a second plane, where the first and second planes are offset by a certain number of degrees from each other.

In one embodiment, the coil includes two or more windings in a first plane and two or more windings in a second plane, where the first and second planes are offset by about 60 degrees from each other.

In one embodiment, the coil is comprised of a radiopaque material.

In one embodiment, the coil is comprised of platinum or a platinum alloy.

In one embodiment, the coil includes a hydrogel core material surrounded by a platinum alloy.

In one embodiment, the coil is comprised of a nitinol wire with a platinum jacket.

In one embodiment, the coil includes a hydrogel core material surrounded by a nitinol wire with a platinum jacket.

In one embodiment, the coil comprises one or more repeating sections. In one example, the coil forms the following pattern of loops, left-to-right: horizontal loop, angled loop, vertical loop, horizontal loop, vertical loop, angled loop, vertical loops, and horizontal loop.

A mandrel used to wind an embolic coil is described. In one embodiment, the mandrel includes mounting elements that are configured as follows (starting from the far or distal end to the closest or proximal end or left-to-right). A first bracket member is positioned with its post member at a rotational orientation of 0 degrees. A second cylinder member is position adjacent to the first bracket member. A third bracket member is positioned with its post member at a rotational orientation of about 60 degrees (i.e., about 60 degrees to the right relative to the first bracket member) and adjacent to the second cylinder member. A fourth cylinder member is positioned adjacent to the third bracket member. A fifth bracket member is positioned with its post member at a rotational orientation of about 0 degrees and adjacent to the fourth cylinder member. A sixth cylinder member is positioned adjacent to the fifth bracket member. A seventh bracket member is positioned with its post member at a rotational orientation of about 60 degrees and adjacent to the sixth cylinder member. The eighth cylinder member is positioned adjacent to the seventh bracket member. Finally, the ninth bracket member is positioned with its post member at a rotational orientation of about 0 degrees and adjacent to the eighth cylinder member. A nut is positioned against the first bracket member and another is positioned against the ninth bracket member.

In one embodiment, the mandrel includes one or more winding sections which are located in a first plane, and one or more regions which are located in a second plane.

In one embodiment, the mandrel includes two or more winding sections which are located in a first plane, and two or more regions which are located in a second plane.

In one embodiment, the mandrel includes two or more winding sections which are located in a first plane, and two or more regions which are located in a second plane, where the second plane is offset by about 60 degrees from the first plane.

In one embodiment, the mandrel comprises one or more repeating sections.

A process and/or method to wind an embolic coil on a mandrel is described. In one embodiment, the process and/or method involves winding a coil over a mandrel with one or more repeating sections. In another embodiment, the process and/or method involves winding a coil over a mandrel with one or more repeating sections and cutting the coil to produce two or more identical sections.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

U.S. Pat. Nos. 9,089,405 and 8,066,036 and U.S. Pub. No. 2011/0184455 disclose complex coil embodiments and manufacturing techniques, and are hereby incorporated by reference in their entirety.

Embolic coils are used for occlusive purposes in the vasculature for various reasons, such as occluding aneurysms, atrial septal defects, patent foramen ovale, left atrial appendage occlusion, patent ductus arteriosus, fistula, arterio-venous malformations, fallopian tube occlusion for the purposes of sterilization, and occlusion in the peripheral vasculature.

Often, different types of coils with different characteristics and shapes are used in different stages of filling a treatment space. In this regard, embolic coils can sometimes be categorized into framing coils, filling coils, and finishing coils. For example, a framing coil is typically first implanted to frame the periphery of the treatment site, a filling coil is often subsequently implanted to fill the treatment site, and a finishing coil is sometimes used at the end of the procedure to fill the small gaps left in the treatment site.

Complex coils are referred to as such since they have three-dimensional shapes and thus are often used as framing coils since the three-dimensional shape is ideal to help anchor the coil. However, complex coils can also be used as an all-in-one embolizing coil at larger treatment sites where there is enough space for the complex geometry of the coil to fill into the space. Complex coils can also be used as filling and/or finishing coils when used in larger spaces.

The embolic coil, in one embodiment, is comprised of a hydrogel core with a coil (e.g., platinum or platinum alloy) wrapped around the core. Hydrogel can be conditioned to volumetrically expand upon exposure to a liquid and is often used with coils to increase their size after exposure to blood. Additionally, some hydrogel formulas trigger expansion at only a predetermined pH, such as the pH of human blood, which allows expansion to be triggered with greater specificity. Since the coil is located around the hydrogel core, the hydrogel's expansion at a treatment site may radially expand the diameter of the coil, increasing its size.

In alternate embodiments, the coil may be composed of radiopaque materials such as rhodium, palladium, rhenium, tungsten, gold, silver, tantalum, and various alloys of these metals. Non-radiopaque materials such as nitinol, stainless steel, or cobalt-chromium may also be used. A radiopaque material may also be used with a non-radiopaque material to provide the coil. Although a non-radiopaque material can be used, a radiopaque metal is preferred to aid in imaging. In other embodiments, no hydrogel is used and the coil is solely comprised of platinum or another similar metal. In another embodiment, the coil is comprised of a hydrogel core with a platinum-coated nitinol wire around it. This embodiment combines the radiopaque benefits of including platinum while offering the cost savings of using less expensive materials for a majority of the coil wire.

In one embodiment, the hydrogel core is conditioned to expand between the coil loops and beyond the diameter of the coil itself. In another embodiment the hydrogel remains contained within the diameter of the coil itself.

As previously discussed, mandrels are often used to wind embolic coils in a desired secondary shape (e.g., patterns of loops, curves, straight portions, and similar shapes) so that this secondary shape can be set or fixed (e.g., via application of heat). Once set, the embolic coil will generally return to the desired secondary shape when in an unconstrained condition.

Figure 1:
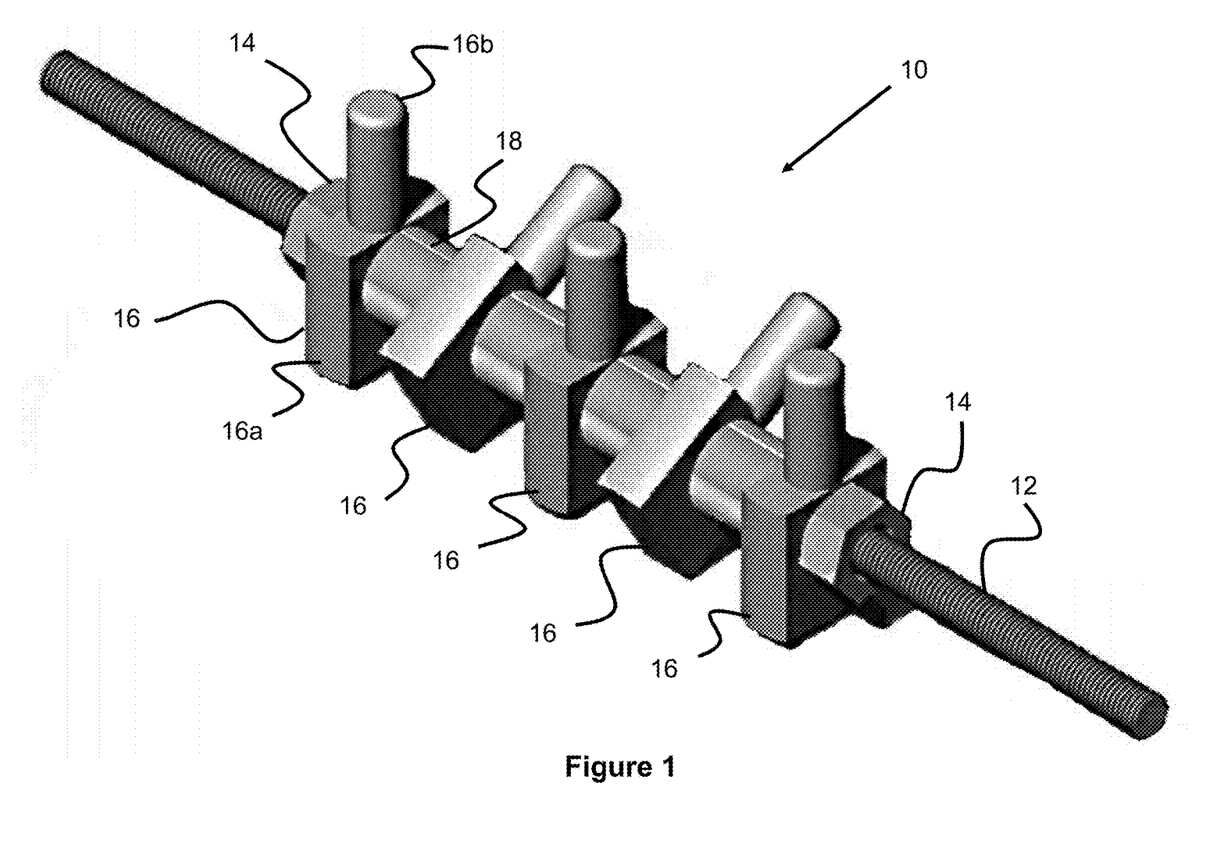
FIG. 1 illustrates a mandrel used to wind an embolic coil.

FIG. 1 illustrates a mandrel 10 used to wind an embolic coil to form a secondary shape. The mandrel 10 includes an elongated member or core 12 that various winding elements are mounted onto. In one embodiment, the core 12 is a threaded, cylindrical screw onto which other components are screwed onto, however, other variations are possible. For example, the core 12 may have a smooth elongated shape that allow other components to slide on and clamp in place.

The mandrel 10 may include one or more mounting elements that fit onto the core 12 and provide various shapes or winding surfaces that are positioned at different orientations on which the embolic coil can be wound. One mounting element is a horizontally positioned cylinder member 18 that includes a threaded passage through which the core 12 passes. Once mounted on the core 12, the rounded portion of the cylinder member 18 generally circumscribes or is positioned around the outer threaded portion of the core 12. The cylinder member 18, while shown as having a cylinder shape (i.e., a circular diameter), can also have a diameter that is ellipsoid, oval, triangular, rectangular, square, or any other shape.

Another mounting element is a bracket member 16 that has a body portion 16a and a post member 16b extending away from the body portion 16a. The body portion 16a preferably has a threaded passage that allows it to be threaded onto the core 12 at various rotational orientations that are generally perpendicular to the axis of the core 12. The body portion 16a is illustrated as having a relative square body, but a variety of shapes are possible, such as circular, cylindrical, rectangular, and triangular. The post member 16b is either fixed to or a unitary portion of the body and is illustrated having a cylindrical shape extending generally perpendicular to the axis of the core 12. Alternately, the post member 12 can have a square shape, oval shape, an ellipsoid shape, a rectangular shape, a triangular shape, an hourglass shape, or other common or irregular shapes, depending on the intended secondary shape of the windings.

In the present example embodiment having a threaded core 12, the mounting elements are kept in a desired orientation by positioning or clamping them against each other. Specifically, one mounting element is threaded to a specific position on the core 12, then another mounting element is threaded tightly against the first mounting element. Once the desired mounting elements are positioned against each other, nut 14 can be threaded onto the proximal and distal ends of the core 12 until each press tightly on the adjacent mounting element. In this respect, the rotational orientation of each mounting element is locked into place.

In one embodiment, the mounting elements may include angle indicia printed on their surfaces. These indicia on a first mounting element allows a user to position an adjacent mounting element at a known, desired angle relative to the first mounting element. Hence, the user can easily determine whether one mounting element is positioned, for example, at 60 degrees relative to an adjacent mounting element.

In one example, a pattern can be created with bracket members 16 having rotational orientations or angles that alternate between a first angle and a second angle, interspersed by cylindrical members. Such a pattern can be increased or decreased in length as desired.

In the specific example of FIG. 1, the mounting elements are configured as follows (starting from left to right). A first bracket member 16 is positioned with its post member 16*b* at a rotational orientation of 0 degrees. A first cylinder member 18 is position adjacent to the first bracket member 16. A second bracket member 16 is positioned with its post member 16*b* at a rotational orientation of about 60 degrees (i.e., about 60 degrees to the right relative to the first bracket member 16) and adjacent to the first cylinder member 18. A second cylinder member 18 is positioned adjacent to the second bracket member 16. A third bracket member 16 is positioned with its post member 16*b* at a rotational orientation of about 0 degrees and adjacent to the second cylinder member 18. A third cylinder member 18 is positioned adjacent to the third bracket member 16. A fourth bracket member 16 is positioned with its post member 16*b* at a rotational orientation of about 60 degrees and adjacent to the third cylinder member 18. A fourth cylinder member 16 is positioned adjacent to the fourth bracket member 16. Finally, a fifth bracket member 16 is positioned with its post member 16*b* at a rotational orientation of about 0 degrees and adjacent to the fourth cylinder member 18. A nut 14 is positioned against the first bracket member 16 and another is positioned against the fifth bracket member 16. In this respect, the embolic coil can be wrapped in loops, one or more times, around each of the bracket members 16 and cylinder members 18.

Figure 2:
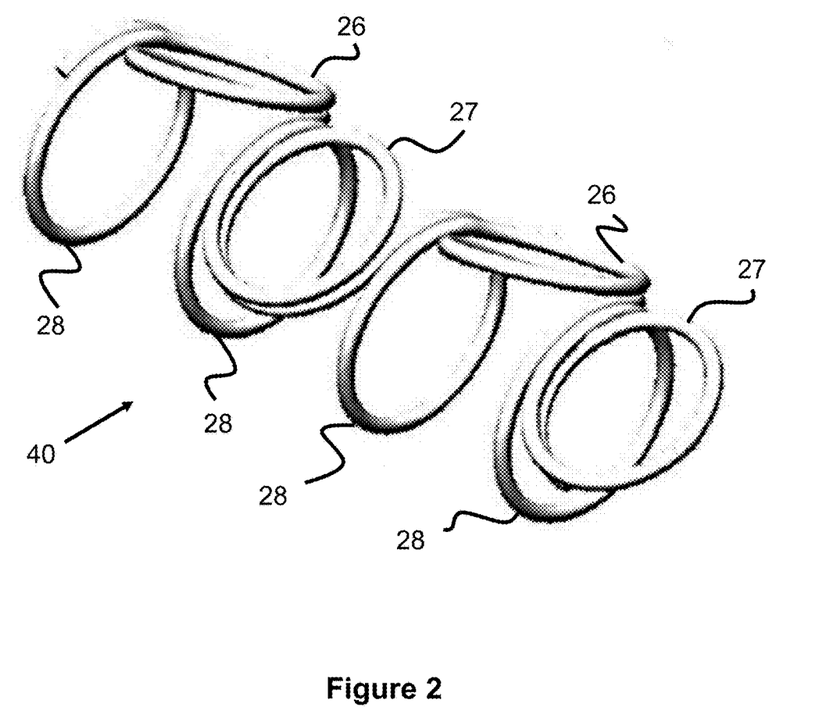
FIG. 2 illustrates an embolic coil comprising eight loops where some loops have an alternate angular offset.

The example of FIG. 1 produces an 8-loop coil seen in FIG. 2. FIG. 2 illustrates an embolic coil 40, including four vertical loops 28, two horizontal loops 27, and two angled loops 26 (e.g., 60 degrees relative to the horizontal loops 28). Embolic coil 40 specifically includes loops (left-to-right): vertical loop 28, horizontal loop 27, vertical loop 28, angled loop 26, vertical loops 28, horizontal loop 27, vertical loop 28, and angled loop 26. This embolic coil 30 can be created on its own on a mandrel 10 as disclosed above, or can be cut from a longer embolic coil.

One advantage to the creation of regularly repeating embolic coil loop patterns is the ability to cut the embolic coils into smaller coils after the secondary shape has been imparted to the coil. For example, a mandrel 10 can be lengthened with the same repeating patterns at specific multiples and them cut accordingly rather than making each coil individually, saving significant manufacturing time. For example, the user can wind an 8-loop coil pattern on the mandrel 10, cut the coil in half, and have two coils with an equal profile remaining instead of separately winding two 4-loop coils. Similarly, a coil can be made with 12, 16, or 20 loops and be trimmed to make multiple identical coils with 4 loops (i.e. 3, 4, or 5). In alternative embodiments, the cuts can come in uneven increments to create multiple coils with different number of loops and different length.

Figure 3:
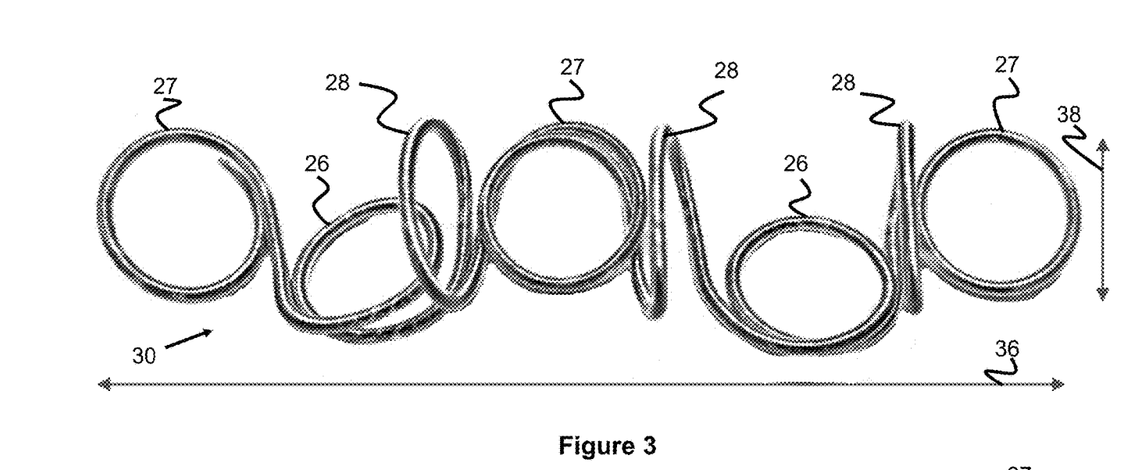
FIG. 3 illustrates an alternative configuration of an embolic coil comprising eight loops of FIG. 2.
Figure 9:
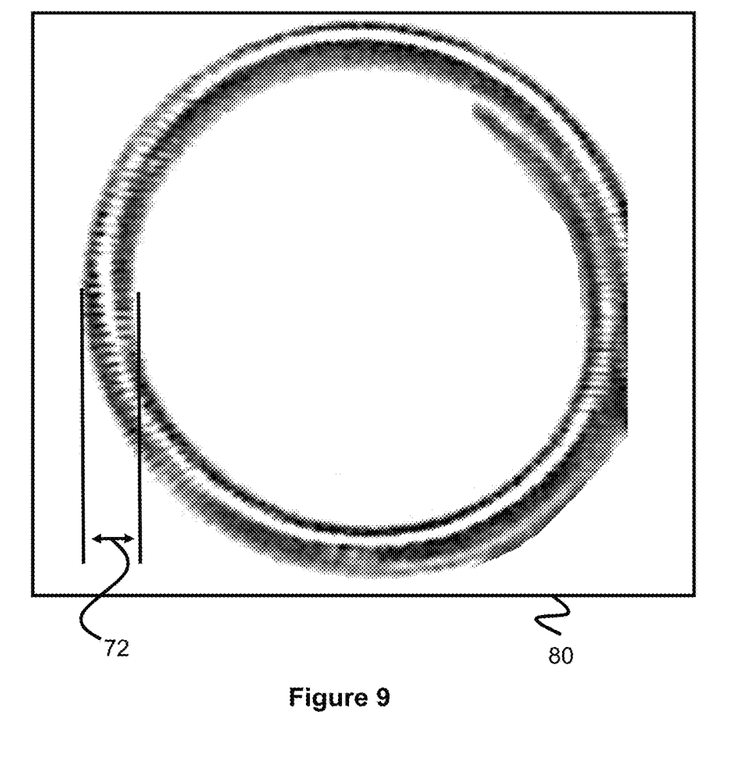
FIG. 9 illustrates a secondary diameter of an embolic coil based on one of the coil loops.

FIG. 3 illustrates an alternative configuration of an embolic coil 30 having an 8-loop secondary structure by making slight modifications to the mandrel 10 in FIG. 1. Generally, this embolic coil 30 is wound on a mandrel 10 configured to create three horizontal loops 27, three vertical loops 28, and two angled loops 26 (e.g., angled at about 60 degrees relative to the horizontal loops 27). Note that the loop angles described in this specification refer to an angle of a plane formed by the loop's horizontal structure, such as plane 80 in FIG. 9. Specifically, FIG. 3 illustrates the following pattern of loops, left-to-right: horizontal loop 27, angled loop 26, vertical loop 28, horizontal loop 27, vertical loop 28, angled loop 26, vertical loops 28, and horizontal loop 27.

Figure 4:
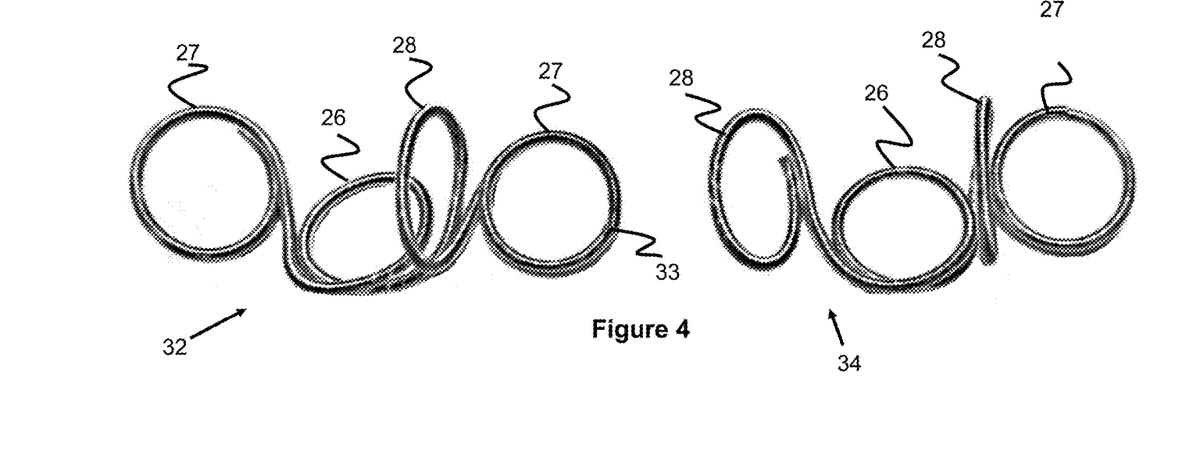
FIG. 4 illustrates the embolic coil of FIG. 3 which can be cut to create two embolic coils comprising four-loops each.
Figure 5:
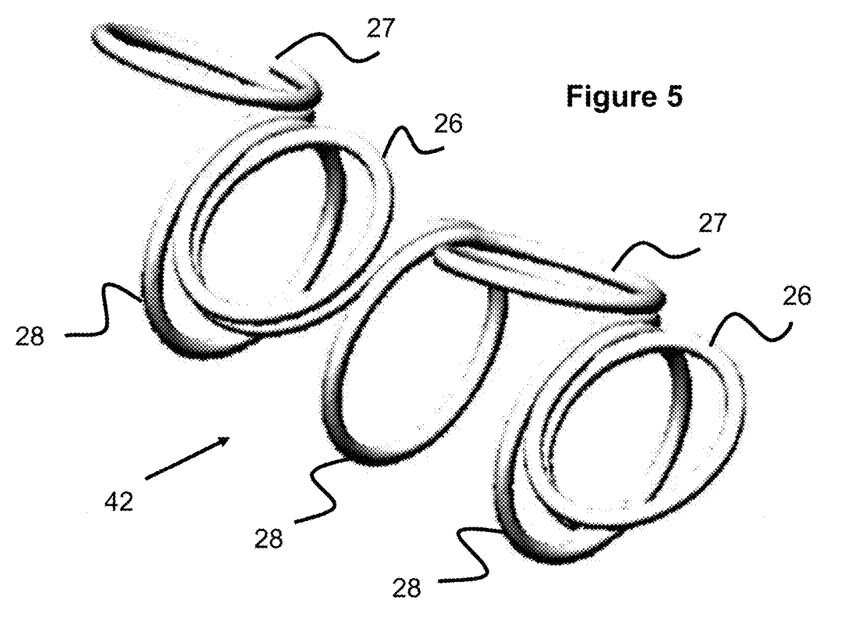
FIGS. 5-8 illustrate embolic coils comprising various numbers of loops where some loops have an alternate angular offset.
Figure 6:
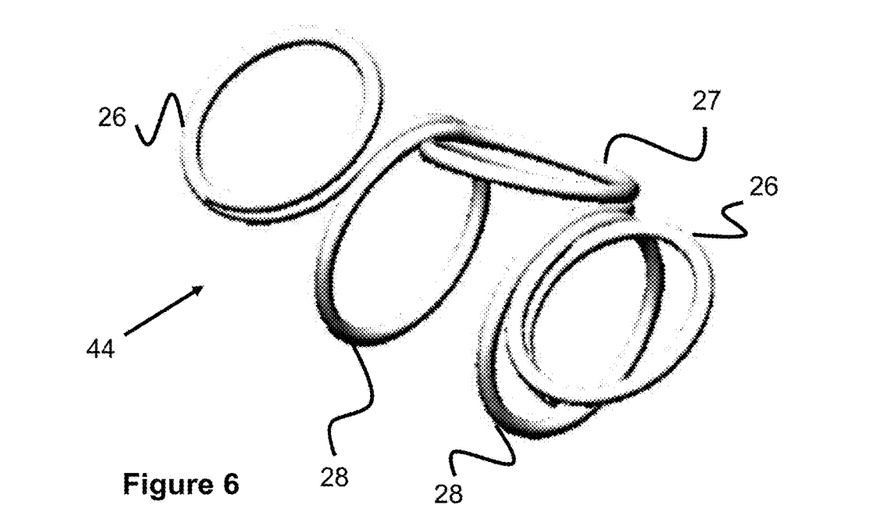
Figure 7:
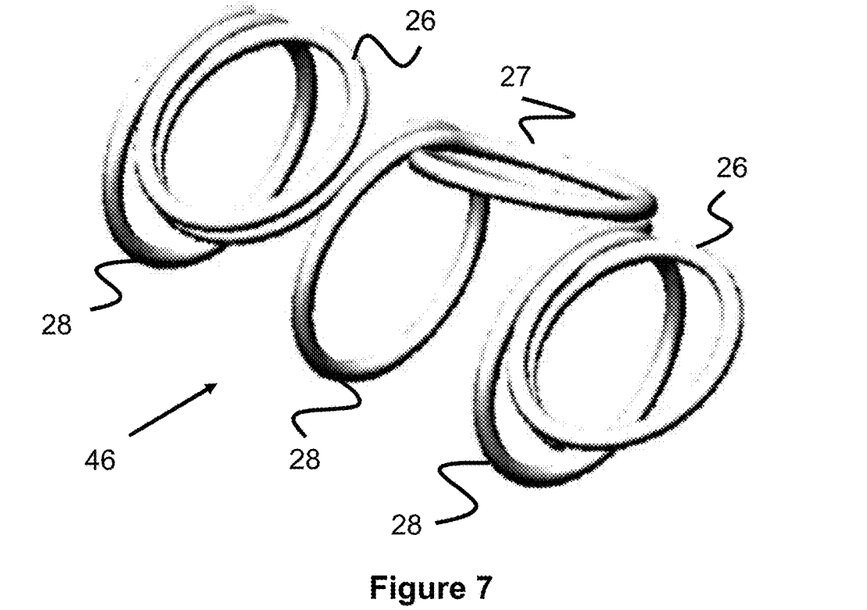

FIG. 4 illustrates the embolic coil 30 of FIG. 3 after being cut at the end of the middle horizontal loop 27 at point 33, forming embolic coil 32 and embolic coil 34. Embolic coil 32 includes loops (left-to-right): horizontal loop 27, angled loop 26, vertical loop 28, and horizontal loop 27. Embolic coil 34 includes loops (left-to-right): vertical loop 28, angled loop 26, vertical loops 28, and horizontal loop 27. In this regard, the two embolic coils 32 and 34 result in substantially less manufacture time.

It should be further understood that the embolic coils 32 and 34 can be made by assembling the mandrel 10 with the appropriate mounting elements to result in the pattern of loops of the embolic coil 30 in FIG. 3. Next, the secondary coil pattern is set (e.g., by heat setting the loops). Finally, the embolic coil 30 is cut at location 33 to result in embolic coil 32 and 34. While location 33 is specified in FIG. 4, this cut location may be moved to other positions, as desired, to create two smaller embolic coils with different patterns.

Figure 8:
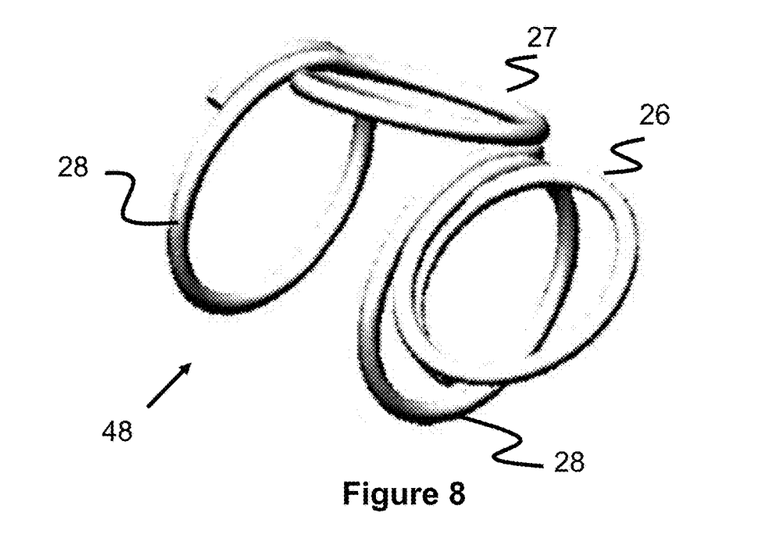

FIGS. 5-8 illustrate embolic coils with similar patterns as those previously described, except with different lengths. As noted earlier, these coils can be created on their own but also by cutting a longer coil of a similar pattern. Embolic coil 42 in FIG. 5 includes three vertical loops 28, two horizontal loops 27, and two angled loops 26. Embolic coil 44 in FIG. 6 includes two vertical loops 28, one horizontal loop 27, and two angled loops 26. Embolic coil 46 in FIG. 7 includes three vertical loops 28, one horizontal loops 27, and two angled loops 26. Embolic coil 48 in FIG. 8 illustrates two vertical loops 28, one horizontal loop 27, and one angled loop 26.

In one example, the loops of these configurations can be formed by winding right-to-left and stopping once the desired number of loops are made. In another example, these loop configurations are made by winding over the full length of the mandrel and cutting the extra loops. The extra loops can be used as shorter coils. Alternate manufacturing configurations may wind left-to-right. Due to the repeatability of the angled offset pattern between the various winding elements, winding in either direction (left-to-right or right-to-left) may produce a substantially similar coil design.

The mandrel can also be expanded to include more winding elements. In one embodiment, a larger mandrel can be used (e.g., more than 9 winding elements) but the mandrel maintains the same profile pattern shown in FIG. 1 in which one alternating set of brackets have one angular orientation and another alternating set of brackets have a different angular orientation. Alternately, the mandrel can include less winding elements.

The loops of the coils and length of the coils of the embodiments disclosed herein can vary in size. In one example, the coil loop diameters 38 (FIG. 3) can range from about 3 mm to about 20 mm. The coil length 36 can vary between about 12 cm to about 40 cm, depending on the number and size of the loops.

In one embodiment, the diameter of all the coil loops is consistent. In another embodiment, the diameter of the coil loops is variable (e.g., progressively increases in diameter, decreases in diameter, or otherwise changes in a non-progressive pattern). In another embodiment the diameter of the loops is different between one or more of the vertical loops 28, horizontal loops 27, and angled loop 26. For example, referring to FIG. 2, the loops increase as you progress from left-to-right. In another embodiment, all the odd-numbered loops have a first, smaller diameter and all the even-numbered loops have a second, larger diameter. For example, the odd numbered loops are all about 3 mm and the even numbered loops are all about 4 mm; or for a larger coil, the odd numbered loops are all about 19 mm and the even numbered loops are all about 20 mm. The diameters of the winding posts can also be individually customized to control the loop diameters.

The loop diameters and variability of the loop diameters (e.g., the difference in diameters between the even-numbered and odd-numbered loops, or the difference in loop diameters between one loop and another loop) can be selected based on the use for the coil. For example, for a framing coil where strong anchor strength is desirable the first loop can be larger than the second loop. In one example, this pattern can continue throughout the coil where the odd numbered loops are larger than the even numbered loops. In another example, the first loop can be larger than the second loop and the rest of the loops have a relatively consistent diameter after that. In another example, the first loop can be larger than the second loop and each successive loop can be smaller still. Alternately, the first loop can be smaller than the second loop to promote more pushability of the coil via less friction at the distal end of the coil assembly. The second loop can then nest over the first coil upon delivery. This embodiment may still function well as a framing coil since the first and second loops may provide good anchor strength to grip the vessel wall.

In one embodiment, the first loop is smaller than the second loop and the odd-numbered loops are smaller than the even-numbered loops. In one embodiment, the difference between the odd-number and even-numbered loops is anywhere from about a 0-25% difference.

The specification has discussed coils and the differences between framing, filling, and finishing coils. The coil described in the various embodiments can be used as an all-in-one coil where the coil itself can be used to occlude the target site without the use of any other coils. Alternately, the coil can be used as a framing coil to frame the target site. Alternately, the coil can be used as a filling coil. In larger treatment sites, the coil can be used as a finishing coil to pack the leftover open space. Thus the coil described in the various embodiments can be used for a variety of purposes.

The coil assumes a secondary or expanded diameter when freed from a delivery catheter, e.g. when pushed into the treatment site. The coil assumes a primary diameter or shape when sheathed linearly in a catheter while being delivered to a treatment site. Thus, the winding diameters described above refer to the secondary diameter, since that is the expanded, shape memory shape the coil will adopt after delivery.

The primary diameter of the coil (width 72 in FIG. 9) is gauged not on the diameter of the mandrel pins used to wind the coil, but the actual thickness of the coil itself since the coil adopts its primary, elongated configuration while sheathed in the catheter. The primary diameter of the coil, in one example, can vary between about 0.018 inches to about 0.029 inches. The coil is typically delivered through a catheter having an inner diameter that is at least equivalent or slightly greater than the primary diameter of the coil, so the coil can be pushed through the catheter. In one example, the coils described in these embodiments can be delivered through a catheter with an inner diameter of about 0.02 inches to about 0.035 inches. These values are only offered as examples and the coils can be scaled up or down in size as needed.

The coils have shape memory imparted to them via a heat treatment process. Thus the coils are heated or annealed into shape over the mandrel after winding. The coils can be anchored or tied to the mandrel so they are in tension. After heating, the coils can be cooled so the shape memory is imparted. The shape memory of the coil is important so the coil readily adopts its secondary configuration after being released from the delivery catheter or microcatheter. Additional example details of a heat setting process (as well as other embolic coil manufacturing details) can be found in U.S. Pat. No. 8,066,036 and U.S. Pub. No. 2011/0184455, both of which are incorporated herein by reference.

The coil loop revolutions can vary based on the desired coil properties. However, a sample configuration is contemplated for illustrative purposes. Referencing FIG. 2 and referring to consecutive loops from right-to-left, loop 1 is wrapped about 450 degrees (about 1.25 revolutions); loops 2, 4, 6, 8 are wrapped about 420 degrees (about 1 and ⅙ revolutions); loop 3, 5, 7 are wrapped about 540 degrees (about 1.5 revolutions). Again, these example revolutions can be applied to other embodiments in this specification in a similar manner.

FIG. 4 shows the eight-loop coil of FIG. 3, which is cut in two to create two four-loop coils. A sample coil configuration for the 4-loop coil configuration would be similar to the 8-coil configuration above (loops 1-4 would be one coil, loops 5-8 would be another coil since the coil is simply cut in half). However, loops 4 and 5 may have a slightly different wind angle since the cut is made between loops 4 and 5. In one example, each of loops 4 and 5 lose ¼ of a revolution and thus loop 4 is wrapped about 330 degrees and loop 5 is wrapped about 450 degrees (about 1.25 revolutions).

The loop revolution/winding angle measurements offered are rough approximations since the starting point for the loop can vary, since the coil is being continuously wound over all the sections of the mandrel.

Please note any figures, measurements, materials, and other similar descriptions are meant to offer illustrative examples of embodiments discussed herein and are not meant to be solely limited to the representations or descriptions. Ranges given and numerical values are meant to be approximations and not limited to the specified values, and such numerical figures are meant to be illustrative in nature and not meant to be overtly limiting.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of creating a secondary shape of an embolic coil, comprising:

providing a mandrel having an elongated core with an axis extending therealong and a plurality of mounting elements disposed on said elongated core, wherein said plurality of mounting elements each comprise a bracket member having a post member extending generally perpendicular to said axis of said elongated core;

providing an embolic coil;

wrapping said embolic coil on said mandrel so as to create a repeating pattern of loops relative to said axis of said elongated core; said pattern consisting essentially of:
- a first horizontal loop positioned at a first angle;
- a first vertical loop directly connected to said first horizontal loop and being positioned at a second angle perpendicular to said first angle;
- a first angled loop directly connected to said first vertical loop; said first angled loop being oriented at a third angle that is between said first and said second angle; and,
- a second vertical loop directly connected to said first angled loop and being positioned at said second angle; and, heat setting said embolic coil so as to impart said repeating pattern in said mandrel as a secondary shape.

2. The method of claim 1, wherein said third angle is about 60 degrees relative to said first angle.

3. The method of claim 1, wherein said repeating pattern further comprises:
- a second horizontal loop connected to said second vertical loop and being positioned at said first angle;
- a third vertical loop connected to said second horizontal loop and being positioned at said second angle.

4. The method of claim 3, wherein said repeating pattern further comprises: a second angled loop connected to said third vertical loop and being angled at said third angle.

5. The method of claim 4, wherein said repeating pattern further comprises: a third horizontal loop connected to said second angled loop and being angled at said second angle.

6. A method of creating a secondary shape of an embolic coil, comprising:

providing an embolic coil;

providing a mandrel having an elongated shape with an axis extending therethrough;

creating one or more of the following pattern, the pattern consisting essentially of:

forming a first horizontal loop with said embolic coil around a first post member that is positioned on said mandrel at a first angle perpendicular to said axis;

forming a first vertical loop that immediately follows said first horizontal loop, with said embolic coil around said axis;

forming a second horizontal loop that immediately follows said first vertical loop, with said embolic coil around a second post member that is positioned on said mandrel at a second angle perpendicular to said axis; said second angle being different from said first angle;

forming a second vertical loop that immediately follows said second horizontal loop, with said embolic coil around said axis; and, heat setting said embolic coil so as to impart said repeating pattern in said mandrel as a secondary shape.

7. The method of claim 6, wherein said second angle is positioned at about 60 degrees relative to said first vertical loop.

8. The method of claim 6, further comprising forming a third horizontal loop with said embolic coil on a third post member that is positioned on said mandrel at said first angle perpendicular to said axis.

9. The method of claim 8, further comprising forming a third vertical loop with said embolic coil around said axis.

10. The method of claim 9, further comprising forming a fourth horizontal loop with said embolic coil on a fourth post member that is positioned on said mandrel at said second angle.

11. A method of creating a secondary shape of an embolic coil, comprising:

providing a mandrel having an elongated shape with an axis extending therealong and a plurality of mounting elements disposed along said elongated shape;

providing an embolic coil;

wrapping said embolic coil on said mandrel so as to create a repeating pattern of loops; said pattern consisting essentially of:
- a first axially-horizontal loop positioned at a first angle parallel to said axis;
- a first vertical loop that immediately follows said first axially-horizontal loop, connected to said first axially-horizontal loop and being positioned around said axis;
- a second axially-horizontal loop that immediately follows said first vertical loop, connected to said first vertical loop; said second axially-horizontal loop being oriented at a second angle parallel to said axis; said second angle being different from said first angle; and,
- a second vertical loop that immediately follows said second axially-horizontal loop, connected to said second axially-horizontal loop and being positioned around said axis; and, heat setting said embolic coil so as to impart said repeating pattern in said mandrel as a secondary shape.

12. The method of claim 11, wherein said mandrel comprises an elongated core with a plurality of brackets mounted thereon, said brackets each having a post extending radially away from said elongated core.

* * * * *